(12) United States Patent
Trantow et al.

(10) Patent No.: US 6,469,503 B2
(45) Date of Patent: Oct. 22, 2002

(54) EDDY CURRENT INSPECTION PROBE AND METHOD OF USE

(75) Inventors: Richard Lloyd Trantow, Depoe Bay, OR (US); Sandie Elizabeth Gresham, Cincinnati, OH (US); Douglas Edward Ingram, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 9 days.

(21) Appl. No.: 09/817,873

(22) Filed: Mar. 26, 2001

(65) Prior Publication Data

US 2002/0135363 A1 Sep. 26, 2002

(51) Int. Cl.[7] .............................................. G01N 27/72
(52) U.S. Cl. ...................... 324/219; 324/219; 324/238
(58) Field of Search ................................ 324/219, 220, 324/237, 238, 239, 240, 241, 242, 243

(56) References Cited

U.S. PATENT DOCUMENTS

| 4,629,984 A | 12/1986 | Scalese |
| 4,668,912 A | 5/1987 | Junker |
| 5,204,622 A | 4/1993 | McCaslin et al. |
| 5,315,234 A | * 5/1994 | Sutton, Jr. et al. .......... 324/234 |
| 5,442,286 A | 8/1995 | Sutton, Jr. et al. |
| 5,903,147 A | 5/1999 | Granger, Jr. et al. |
| 6,339,326 B1 | * 1/2002 | Trantow ..................... 324/219 |

FOREIGN PATENT DOCUMENTS

| EP | 0 095 845 A1 | 12/1983 |
| EP | 0 348 739 A1 | 1/1990 |
| EP | 0 577 244 A2 | 1/1994 |
| EP | 1 202 053 A1 | 5/2002 |

* cited by examiner

*Primary Examiner*—Edward Lefkowitz
*Assistant Examiner*—Subhash A Zaveri
(74) *Attorney, Agent, or Firm*—V. Ramaswamy; Sonnenschein, Nath & Rosenthal

(57) ABSTRACT

An eddy current inspection probe for inspecting a preselected surface at least partially defining an opening in a component. The probe includes a cast core having an exterior surface sized and shaped for receipt within the opening of the component and an eddy current array positioned over the exterior surface of the core for generating and detecting magnetic fields in the component to inspect the preselected surface of the component.

14 Claims, 6 Drawing Sheets

EDDY CURRENT INSPECTION PROBE AND METHOD OF USE

The United States government has rights in this invention under Contract No. N00019-96-C-00080 awarded by the Department of the Navy.

BACKGROUND OF THE INVENTION

The present invention relates generally to eddy current inspection probes for inspecting a surface of a manufactured component, and more particularly to a probe having an improved fit with the surface of the component.

Eddy current inspection is commonly used to detect flaws in surfaces of manufactured components such as gas turbine engine components. During this type of inspection, electromagnetic induction is used to induce eddy currents in the component being inspected. An array of coils inside an eddy current probe generates alternating magnetic fields which induce the eddy currents in the component when the probe is moved near the component. When flaws are present in the component, the flow of eddy currents is altered. The altered eddy currents produce changes in a secondary magnetic field which are detected by the array of coils inside the eddy current probe. The array generates an electrical signal in response to the altered secondary magnetic field. The amplitude of the electrical signal is generally proportionate to the size of the flaw. Thus, approximate sizes and general locations of flaws, may be determined using eddy current probes.

The array must be kept at a constant distance from the surface of the component being inspected to ensure the amplitude of the electrical signal is proportionate to flaw size. One way of ensuring a constant distance is by sizing and shaping the probe substantially identically to the feature being inspected. For instance, if the surface of an opening in a gas turbine engine disk such as a dovetail slot bottom is being inspected, a probe sized and shaped substantially identically to the opening is used.

Frequently, the probe is made to collapse so it can fit into the opening. These collapsible probes generally have an expandable core inside a flexible covering which holds the array. In the past, the covering was bonded to the core. As a result, the covering stretched and distorted as it expanded. Changes in the probe shape prevented the array from being positioned at a uniform distance from the surface being inspected. Further, due to variations in size and shape of the actual features being inspected, gaps sometimes occurred between the probe and the surface which also prevented the array from being positioned at a uniform distance from the surface being inspected.

SUMMARY OF THE INVENTION

Among the several features of the present invention may be noted the provision of an eddy current inspection probe for inspecting a preselected surface at least partially defining an opening in a component. The eddy current inspection probe comprises a cast core having an exterior surface sized and shaped for receipt within the opening of the component. The core is resiliently deformable between a retracted position for inserting the probe into and removing the probe from the opening in the component and an expanded position in which the probe is sized and shaped for at least partially filling the opening and contacting the preselected surface of the component for inspecting the surface. Further, the probe includes an eddy current array positioned over the exterior surface of the core for generating and detecting magnetic fields in the component to inspect the preselected surface of the component. The eddy current array has an outer surface shaped substantially identically to the preselected surface of the component when the core is in the expanded position for maintaining the outer surface of the array a preselected distance from the surface of the component.

In another aspect, the present invention includes a method of making a core for an eddy current inspection probe. A polyurethane epoxy is mixed and poured into a mold shaped for producing the core. The mold is opened after a period of time sufficient for the epoxy to cure, and the core is removed from the mold.

In yet another aspect of the present invention a core having an exterior surface sized and shaped for receipt within the opening of the component is molded, and an element is positioned over the exterior surface of the core. A compliant covering is positioned over an outer face of the element. An eddy current array is positioned over the covering for generating and detecting magnetic fields in the component to inspect the preselected surface of the component.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
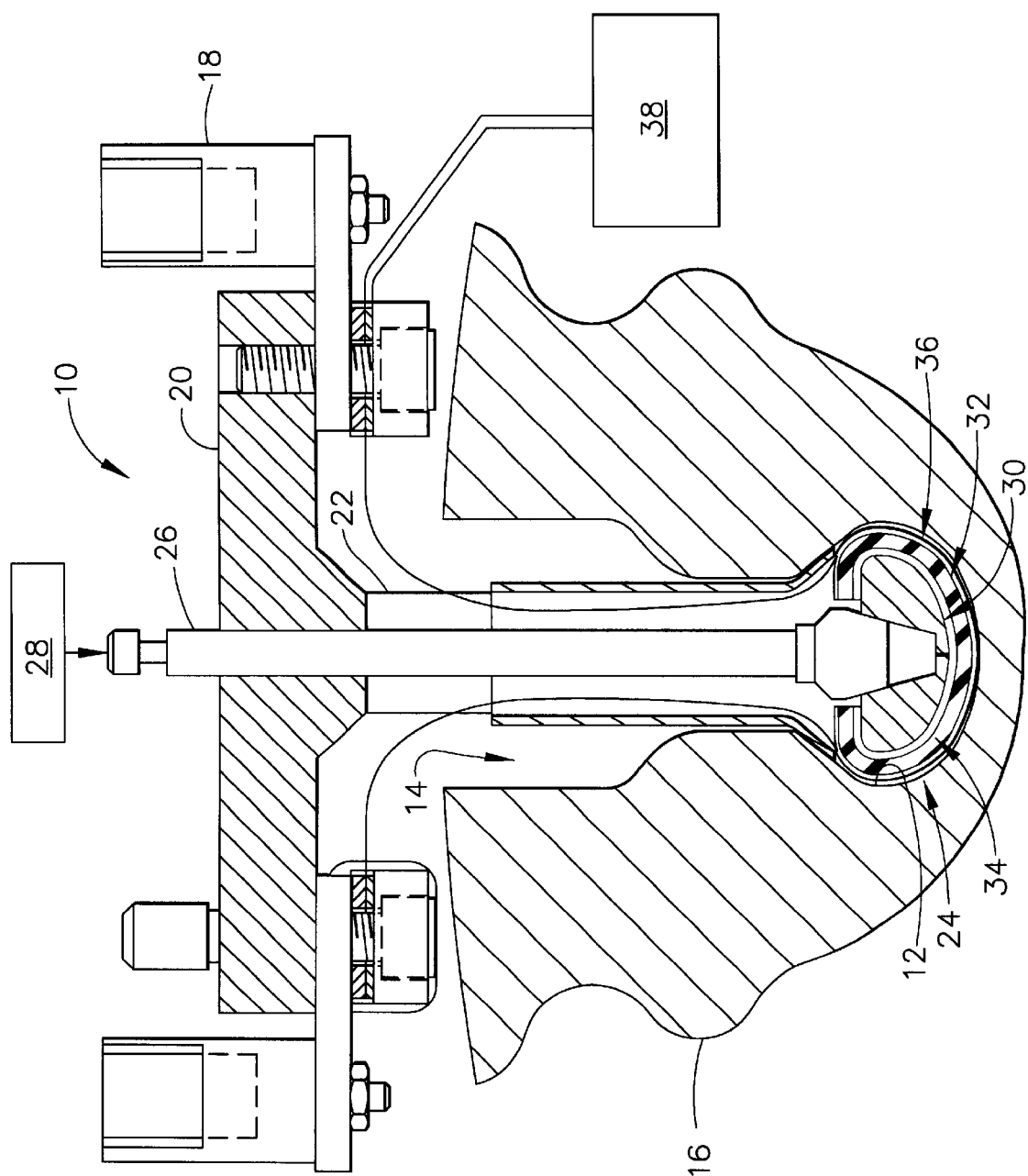
FIG. 1 is a vertical cross section of an eddy current inspection probe of the present invention shown in an opening of a component.

Referring now to the drawings and in particular to FIG. 1, an eddy current inspection probe of the present invention is designated in its entirety by the reference number 10. The probe 10 is sized and shaped for inspecting a preselected surface 12 (e.g., a dovetail slot bottom of a gas turbine engine disk) at least partially defining an opening, generally designated by 14, in a component 16 (partially shown in FIG. 1). The probe 10 is mounted on a conventional fixture 18 positioned adjacent the component 16 to be inspected.

Figure 2:
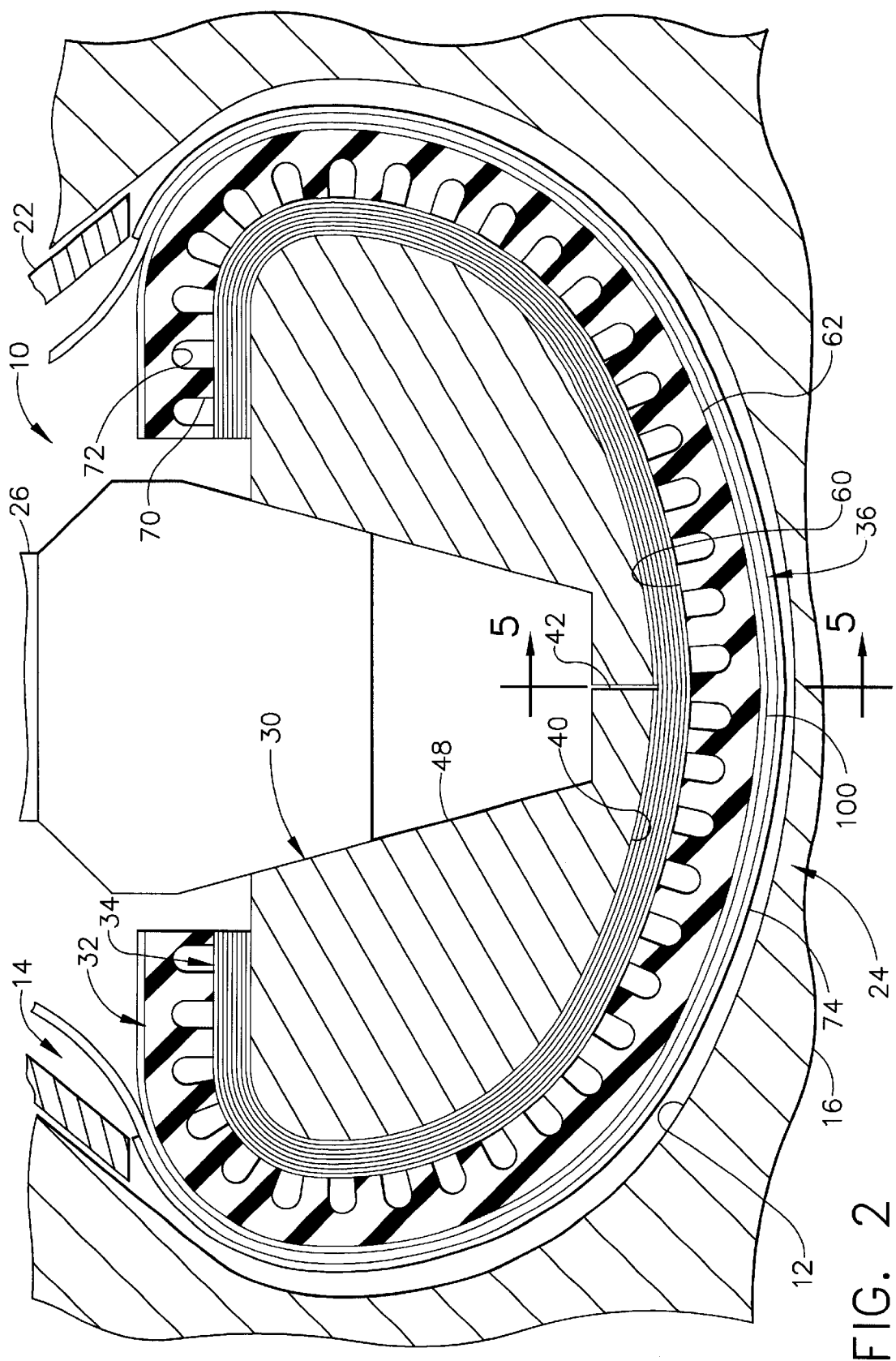
FIG. 2 is a detail of the probe and component showing the probe in a contracted position.
Figure 3:
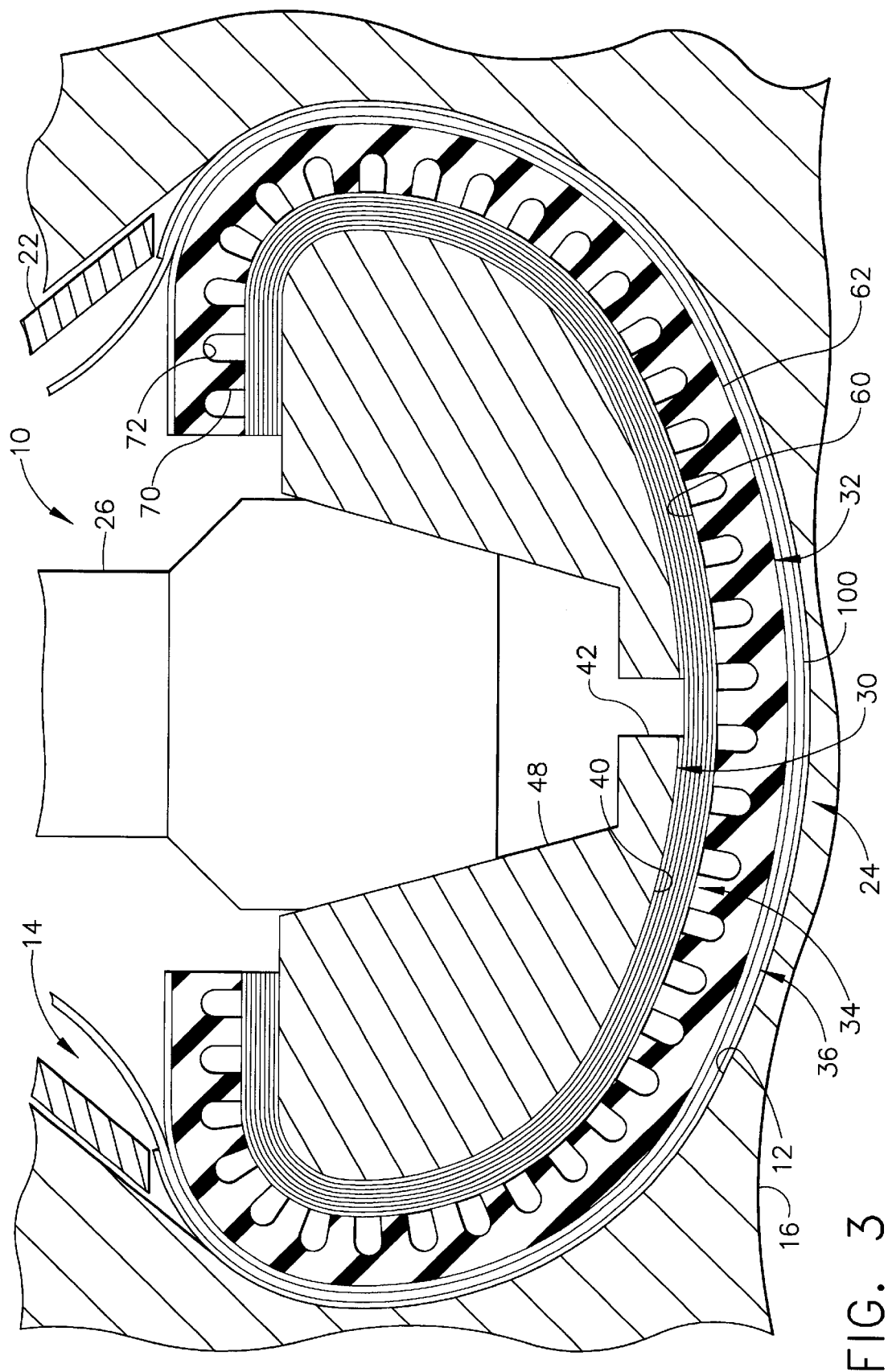
FIG. 3 is a detail similar to FIG. 2 showing the probe in an expanded position.

The probe 10 generally comprises a base 20 which is mounted on the fixture 18, a support 22 extending downward from the base, a head (generally designated by 24) and an actuation rod 26 extending downward through the support. The rod 26 is operatively connected to a conventional actuator 28 for moving the head 24 between a retracted position as shown in FIG. 2 and an expanded position as shown in FIG. 3. As illustrated in FIG. 2, the head 24 comprises a core (generally designated by 30), a compliant covering (generally designated by 32), a layered element (generally designated by 34) positioned between the core and the covering, and an eddy current array (generally designated by 36). As shown in FIG. 1, the eddy current array 36 is connected to a conventional eddy current instrument 38 for providing an output related to flaw size in the surface 12 of the component 16.

Figure 4:
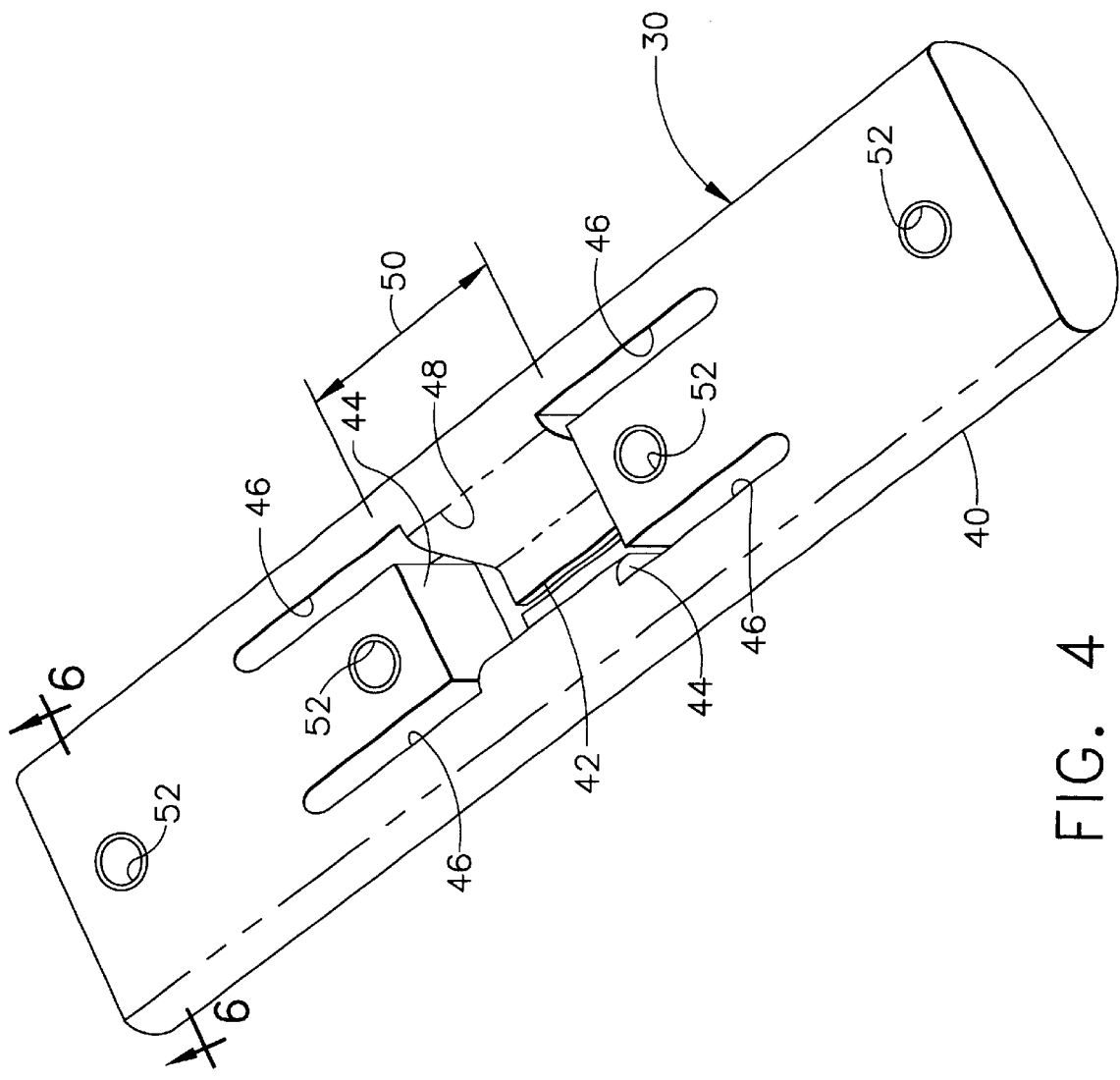
FIG. 4 is a perspective of a core of the probe.
Figure 5:
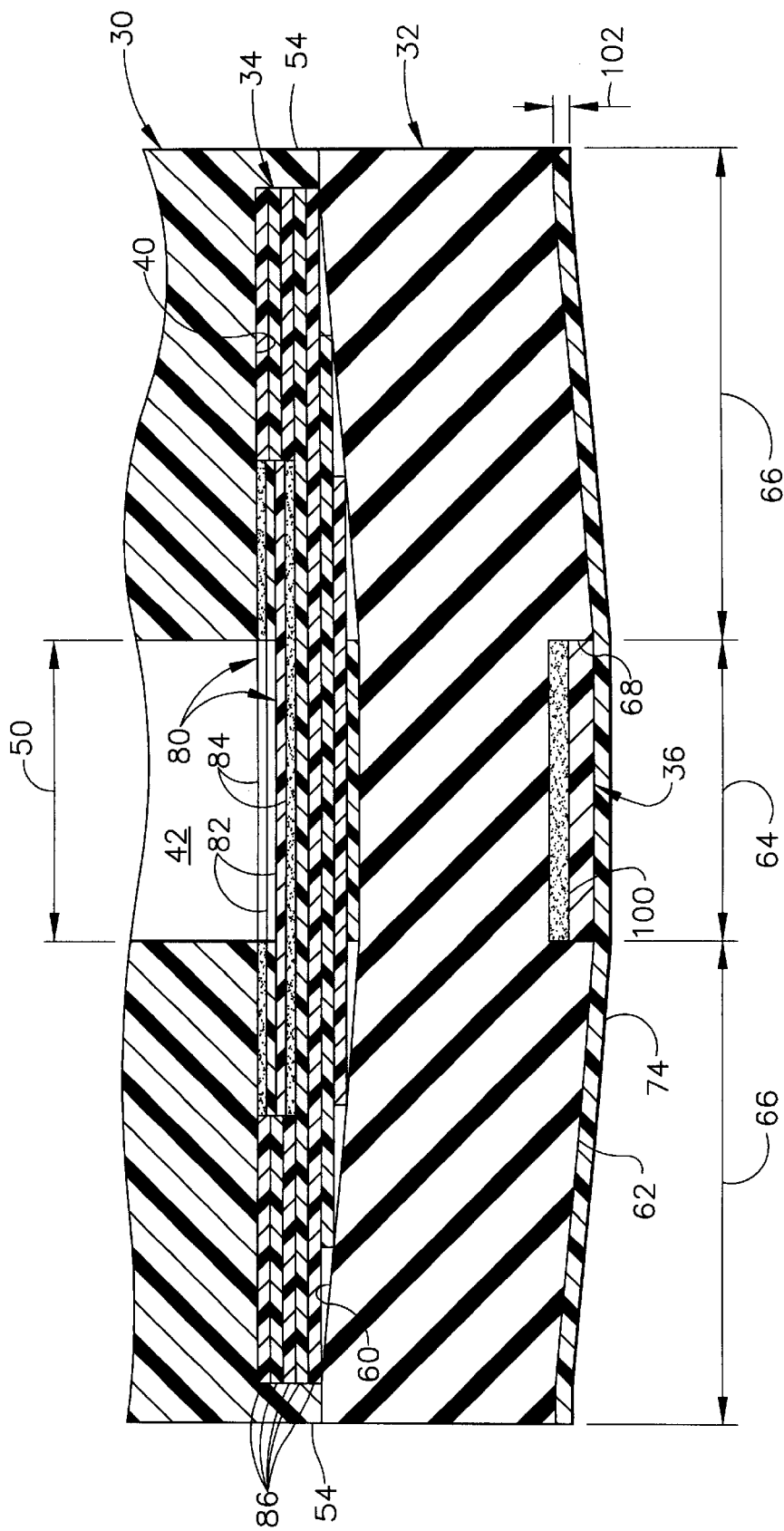
FIG. 5 is a cross section of the probe taken in the plane of line 5—5 of FIG. 2.

As shown in FIG. 2, the core 30 has an exterior surface 40 sized and shaped for receipt within the opening 14 of the component 16. As illustrated in FIG. 4, the core 30 has a centrally located slot 42 which intersects two lateral slots 44 which each intersect two longitudinal slots 46. In addition, a wedge-shaped opening 48 is provided above the central slot 42 for receiving the actuation rod 26. The slots 42, 44, 46 give a central portion 50 of the core 30 flexibility so the core can be moved between a retracted position (illustrated in FIG. 2) for inserting the probe 10 into and removing the probe from the opening 14 in the component 16 and an expanded position (illustrated in FIG. 3) in which the probe is sized and shaped for at least partially filling the opening and contacting the preselected surface 12 of the component for inspecting the surface. Although the central portion 50 of the core 30 may have other lengths without departing from the scope of the present invention, the central portion of one embodiment has a length generally equal to the width of the eddy current array 36 as shown in FIG. 5. Although the core 30 may be made of other materials without departing from the scope of the present invention, the core of one embodiment is molded from semi-rigid polyurethane, such as Easyflo 60 available from Polytek Development Corporation of Easton Pa. Further, although the core 30 may have other hardnesses without departing from the scope of the present invention, the core of one embodiment has a Type D durometer hardness of between about 60 and about 71, and more particularly a Type D durometer hardness of about 65. As further illustrated in FIG. 4, the core 30 may include threaded inserts 52 for attaching the core to the support 22. As illustrated in FIG. 5, end margins 54 of the core 30 protrude outward from the exterior surface 40 of the core and are attached to the covering 32 to prevent the covering from becoming detached from and sliding over the core 30 due to shearing forces as the probe 10 is inserted in the opening 14 and/or drawn over the surface 12 selected for inspection.

The covering 32 is positioned over the exterior surface 40 of the core 30 such that an inner face 60 of the covering faces the core. The covering 32 also has an outer face 62 opposite the inner face 60. The outer face 62 has a central portion 64 and opposite end portions 66 extending longitudinally outward from the central portion. As illustrated in FIG. 5, a groove 68 is provided in the central portion 64 of the outer face 62 for receiving the eddy current array 36. As illustrated in FIG. 2, the inner face 60 of the covering 32 includes longitudinal ribs 70 separated by longitudinal slots 72. Although the covering may be made of other materials without departing from the scope of the present invention, the covering 32 of one embodiment is molded from polyurethane.

As illustrated in FIG. 5, the eddy current array 36 is positioned over the central portion 64 and within the groove 68 in the outer face 62 of the covering 32. The array 36 is adhesively bonded to the bottom of the groove 68 in the covering 32. The array 36, which is conventional, generates and detects magnetic fields in the component 16 to inspect the preselected surface 12 of the component. The eddy current array 36 has an outer surface shaped substantially identically to the preselected surface 12 of the component 16 when the core 30 is in the expanded position for contacting the probe 10 with the preselected surface of the component. A sacrificial sheet of protective material 74 having a low coefficient of friction (e.g, a polytetrafluoroethylene sheet) is adhesively bonded to the outer surface of the array 36 and the outer face 62 of the covering 32 to permit the probe 10 to easily slide across the preselected surface 12 of the component 16 as it is inserted in the opening 14 and removed from the opening. Although the sheet 74 may be made of other materials without departing from the scope of the present invention, the sheet of one embodiment is Teflon7 polytetrafluoroethylene tape having a nominal thickness of about 0.0045 inches. Teflon7 is a federally registered trademark of E.I. du Pont de Nemours and Company of Wilmington, Del.

As further illustrated in FIG. 5, the element 34 is positioned between the exterior surface 40 of the core 30 and the inner face 60 of the covering 32. The element 34 has a laminated construction formed by a plurality of layers of sheet material. Two of the layers, generally designated by 80, have a coefficient of friction selected to permit the inner face 60 of the covering 32 to move tangentially with respect to the exterior surface 40 of the core 30 as the actuation rod 26 moves the core from the retracted position to the expanded position. In other words, these two layers 80 are slick thereby permitting the covering 32 to slide with respect to the core 30 so the covering does not distort from its intended shape as the core expands into the opening 14 of the component 16. This ensures intimate contact between the probe 10 and the preselected surface 12 of the component 16 being inspected. Although the two layers 80 may be made of other materials without departing from the scope of the present invention, the layers of one embodiment are Teflon7 polytetrafluoroethylene tape having a nominal thickness of about 0.0045 inches. Each layer of tape comprises a flexible sheet of polytetrafluoroethylene 82 and an adhesive layer 84. One adhesive layer 84 bonds the respective sheet 82 to the exterior surface 40 of the core 30, and the other adhesive layer bonds the respective sheet to the inner face 60 of the covering 32. Thus, the polytetrafluoroethylene sheets 82 face one another so the sheets are free to move tangentially with respect each other. As will be appreciated by those skilled in the art, the polytetrafluoroethylene tape layers have a low coefficient of friction allowing the layers to slip tangentially with respect to each other. Further, these layers do not extend the full length of the probe 10 so the cover 32 is longitudinally retained on the core 30. In one embodiment, these layers only extend over the length of the slotted region of the core 30.

The element 34 also includes several probe shaping layers of compressibly resilient material 86. As illustrated in FIG. 5, more layers of material 86 underlie the central portion 64 of the cover 32 than underlie the opposite end portions 66 of the covering. As a result, the central portion of the element 34 is thicker than the end portions and the central portion of the outer face 60 of the covering 32 and the array 36 are raised above the end portions of the outer face of the covering. This ensures a tight fit between the array 36 and the surface 12 being inspected but tapers the exterior surface 40 of the cover for easing insertion of the central portion of the covering and the array into the opening. Although the layers of compressibly resilient material 86 may be made of other materials without departing from the scope of the present invention, the layers of one embodiment are made of Kapton7 tape having a nominal thickness of about 0.003 inches. Kapton is a federally registered trademark of E.I. du Pont de Nemours and Company. The adhesive layer of the Kapton7 tape provides the layered element 34 with its compressible resilience.

Figure 6:
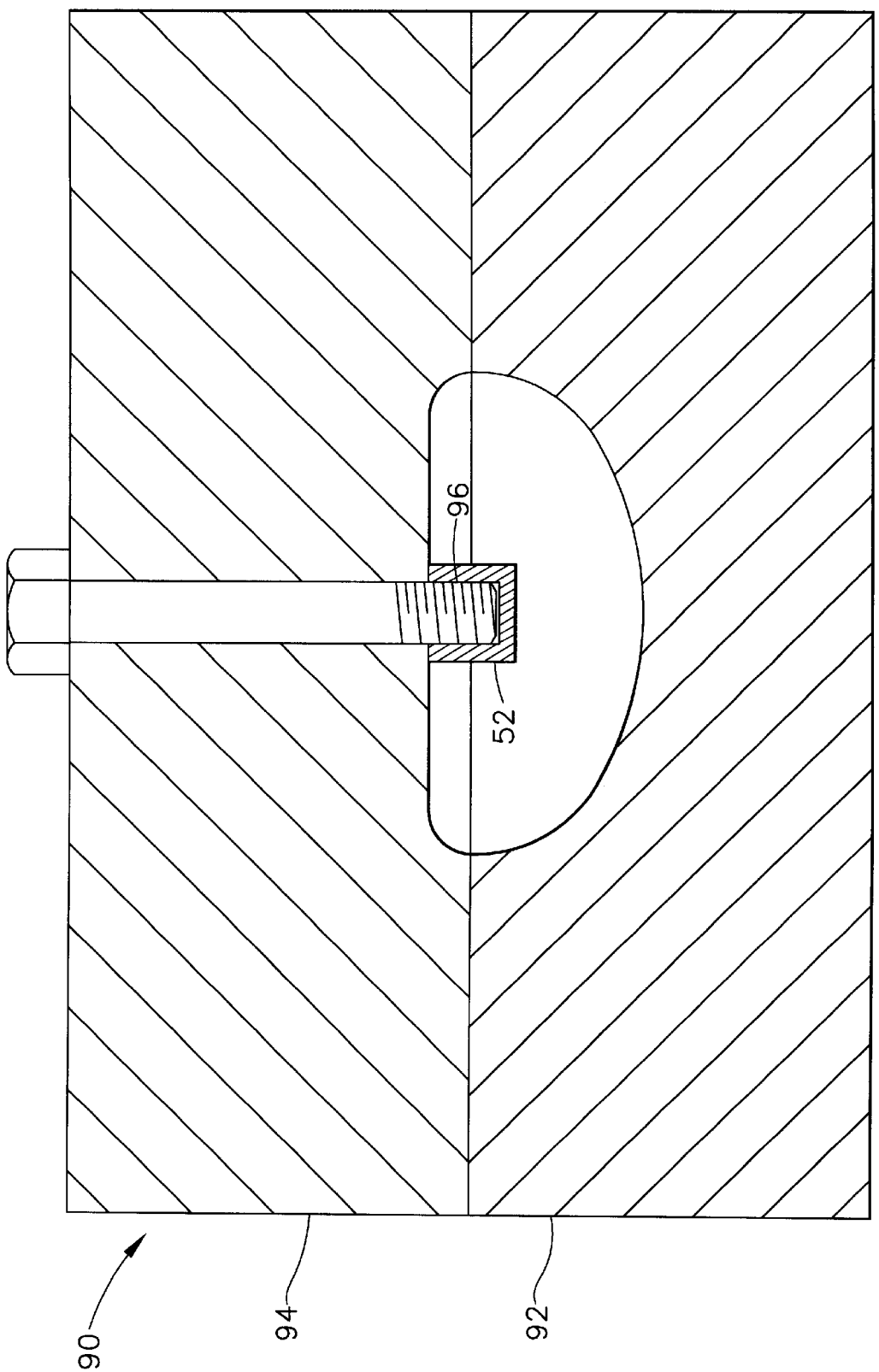
FIG. 6 is a cross section of a mold for casting the core of the probe taken in the plane of line 6—6 of FIG. 4.

Prior to assembling the probe 10 described above, the core 30 is cast. Although the probe 10 may be cast from other materials without departing from the scope of the present invention, in one embodiment the probe 10 is cast from an elastomer such as a polyurethane or a silicone rubber. In one embodiment, an Easyflo 60 polyurethane epoxy is mixed by hand for between about 45 seconds and about one minute. The mixed epoxy is poured into a mold, generally designated by 90, formed by married mold halves 92, 94 as illustrated in FIG. 6 shaped for producing the core 30. Although it is envisioned that other mold releases may be applied to the mold halves 92, 94 before the epoxy is poured into them (or alternatively, that no mold releases are used), in one embodiment a dry mold release agent is used on the mold 90. Although other dry mold release agents may be used without departing from the scope of the present invention, in one embodiment a MS-122DF PTFE Release Agent—Dry Lubricant available from Miller-Stephenson Chemical Company, Inc. of Morton Grove, Ill., is sprayed in the mold 90. Prior to pouring the epoxy into the mold 90, the threaded inserts 52 are positioned on threaded posts 96 on the upper mold half 94 so the inserts join with the core 30 as the epoxy cures.

The epoxy is allowed to cure before the halves 92, 94 are separated. Although the epoxy may be allowed to cure for other periods of time without departing from the scope of the present invention, in one embodiment the epoxy is cured for between about fifteen minutes and about thirty minutes before the core 30 is removed. It is envisioned that it may be desirable to allow the epoxy to cure for about twenty minutes before separating the halves 92, 94 of the mold 90. Although the mold 90 may be maintained at other temperatures without departing from the scope of the present invention, in one embodiment the halves 92, 94 are maintained at about 70 degrees Fahrenheit while the mold halves are married and the epoxy is cured. After the epoxy is cured, the mold 90 is opened and the core 30 is removed from the mold 90. Once the core 30 is removed from the mold 90, the slots 42, 44, 46 are machined in the core. Although other methods of forming the slots 42, 44, 46 may be used without departing from the scope of the present invention, in one embodiment the slots are machined using conventional machining techniques. Alternatively, it is envisioned that the slots 42, 44, 46 may be cast into the core. Although other methods of forming the wedge-shaped opening 48 may be used without departing from the scope of the present invention, in one embodiment the opening is cast in the core. Alternatively, it is envisioned that the opening 48 may be machined using conventional machining techniques.

To assemble the probe 10, the first layer 80 is bonded to the cast core 30, and cut along lines corresponding to the slots 42, 44, 46 in the core 30. Three probe shaping layers 86 are applied to each end of the core 30 adjacent the first layer 80. The second layer 80 is applied face-to-face over the first layer and held in place while the fourth probe shaping layer 86 is applied. The remaining layers 86 are applied to achieve the desired profile of the probe 10 as shown in FIG. 5. Alternatively, it is envisioned that the layers 86 could be eliminated and/or replaced by a separately cast or machined element attached to the layers 80 by an adhesive or other conventional means. The ribbed covering 32 is positioned over and bonded to the layers 86. The end margins 54 of the core 30 are cast in place by applying a limited amount of polyurethane material over the ends of the layers 86 and allowing it to cure. A limited amount of polyurethane material is used to fill the end margins 54 to prevent it from filling the slots 72 between the ribs 70 in the covering 30 in the area over the layers 80. The array 36 is bonded in the slot 42 of the covering using transfer tape 100, and the sheet of material 74 is applied to the outer face 62 of the covering 32.

Preferably, the probe 10 is constructed so that when the core 30 is in the retracted position, the outer surface of the sheet of protective material 32 is sized and shaped substantially identically to a nominal opening 14 for which the probe is made. Thus, when the core 30 is moved to the expanded position, the eddy current array 36 is maintained at a preselected distance 102 from the surface 12 of the component 16.

Once assembled, the probe 10 may be used in a conventional manner. First, the probe 10 is positioned in the opening of the component adjacent the surface to be inspected. After being so positioned, the core 30 of the probe 10 is expanded by moving the actuation rod 26 to the position shown in FIG. 3 to at least partially fill the opening with the probe. As the core expands, the probe 10 contacts the preselected surface of the component so the outer surface of the array 36 remains at a preselected distance from the surface of the component. When the array 36 is in this position, it is energized to generate and detect magnetic fields in the component to inspect the preselected surface of the component in a conventional manner such as by drawing the probe through the slot being inspected. After the eddy current inspection is completed, the core 30 may be moved to a retracted position as shown in FIG. 4 for removing the probe 10 from the opening in the component.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An eddy current inspection probe for inspecting a preselected surface at least partially defining an opening in a component, said eddy current inspection probe comprising:

a cast core having an exterior surface sized and shaped for receipt within the opening of the component, the core being resiliently deformable between a retracted position for inserting the probe into and removing the probe from the opening in the component and an expanded position in which the probe is sized and shaped for at least partially filling the opening and contacting the preselected surface of the component for inspecting the surface; and an eddy current array positioned over the exterior surface of the core for generating and detecting magnetic fields in the component to inspect the preselected surface of the component, the eddy current array having an outer surface shaped substantially identically to the preselected surface of the component when the core is in the expanded position for maintaining the outer surface of the array a preselected distance from the surface of the component.

2. A probe as set forth in claim 1 further comprising a compliant covering positioned between the exterior surface of the core and the eddy current array having an inner face facing the core and an outer face opposite the inner face.

3. A probe as set forth in claim 2 further comprising an element positioned between the exterior surface of the core and the inner face of the covering having a coefficient of friction selected to permit the inner face of the covering to move tangentially with respect to the exterior surface of the core as the core is moved from the retracted position to the expanded position to ensure intimate contact between the probe and the preselected surface of the component being inspected.

4. A probe as set forth in claim 1 wherein the cast core has a Type D durometer hardness of between about 60 and about 71.

5. A probe as set forth in claim 4 wherein the cast core has a Type D durometer hardness of about 65.

6. A probe as set forth in claim 1 wherein the cast core is made from an elastomer.

7. A probe as set forth in claim 1 wherein the elastomer is a polyurethane.

8. A method of using an eddy current inspection probe to inspect a preselected surface at least partially defining an opening in a component, said method comprising the steps of:

molding a core having an exterior surface sized and shaped for receipt within the opening of the component;

positioning an element over the exterior surface of the core having an inner face facing the core and an outer face opposite the inner face;

positioning a compliant covering over the outer face of the element;

positioning an eddy current array over the covering for generating and detecting magnetic fields in the component to inspect the preselected surface of the component;

positioning the probe in the opening of the component; and energizing the eddy current array to generate and detect magnetic fields in the component to inspect the preselected surface of the component.

9. A method of using an eddy current inspection probe as set forth in claim 8, wherein the step of molding the core comprises the steps of:

mixing a polyurethane epoxy;

pouring said mixed epoxy into a mold shaped for producing the core;

opening the mold after the epoxy is substantially cured; and removing the core from the mold.

10. A method as set forth in claim 9 further comprising the step of machining slots in the molded core to permit the core to resiliently deform between a retracted position and an expanded position.

11. A method as set forth in claim 9 further comprising the step of positioning at least one insert in at least one of said mold halves prior to pouring said mixed epoxy into the mold to join said insert with the core.

12. A method as set forth in claim 9 wherein a dry mold release agent is applied to the mold prior to pouring said mixed epoxy into the mold.

13. A method as set forth in claim 8 further comprising the step of expanding the core of the probe after the probe is positioned in the opening of the component to at least partially fill the opening with the probe, to contact the probe with the preselected surface of the component, and to maintain the outer surface of the array a preselected distance from the surface of the component.

14. A method as set forth in claim 13 further comprising the step of moving the core to a retracted position for removing the probe from the opening in the component after the preselected surface is inspected.

\* \* \* \* \*